United States Patent
Dang et al.

(10) Patent No.: US 10,932,707 B2
(45) Date of Patent: Mar. 2, 2021

(54) INTELLIGENT PORTABLE HEALTH MONITORING APPARATUS

(71) Applicant: ARNUXON PHARM-SCI CO., LTD., Beijing (CN)

(72) Inventors: Zhijing Dang, Beijing (CN); Guangteng Wu, Beijing (CN); Liankai Dang, Beijing (CN)

(73) Assignee: ARNUXON PHARM-SCI CO., LTD., Beijing (CN)

( * ) Notice: Subject to any disclaimer, the term of this patent is extended or adjusted under 35 U.S.C. 154(b) by 230 days.

(21) Appl. No.: 16/304,843

(22) PCT Filed: May 22, 2017

(86) PCT No.: PCT/CN2017/085360
§ 371 (c)(1),
(2) Date: Nov. 27, 2018

(87) PCT Pub. No.: WO2017/215409
PCT Pub. Date: Dec. 21, 2017

(65) Prior Publication Data
US 2019/0328293 A1    Oct. 31, 2019

(30) Foreign Application Priority Data
Jun. 13, 2016    (CN) .......................... 201610412703.4

(51) Int. Cl.
*A61B 5/1455*    (2006.01)
*A61B 5/00*    (2006.01)
(Continued)

(52) U.S. Cl.
CPC ........ *A61B 5/14552* (2013.01); *A61B 5/0059* (2013.01); *A61B 5/02427* (2013.01);
(Continued)

(58) Field of Classification Search
CPC ............. A61B 5/14552; A61B 5/0059; A61B 5/02427; A61B 5/14532; A61B 5/6824;
(Continued)

(56) References Cited

U.S. PATENT DOCUMENTS

| 6,546,267 B1 | 4/2003 | Sugiura et al. |
| 2003/0100840 A1 | 5/2003 | Sugiura et al. |

(Continued)

FOREIGN PATENT DOCUMENTS

| CN | 1544947 | 11/2004 |
| CN | 103784150 | 5/2014 |

(Continued)

OTHER PUBLICATIONS

International Search Report of International Application No. PCT/CN2017/085360 dated Aug. 25, 2017.

*Primary Examiner* — Eric F Winakur
*Assistant Examiner* — Abid A Mustansir
(74) *Attorney, Agent, or Firm* — Ping Wang; Morris Manning & Martin LLP

(57) ABSTRACT

The present invention is directed to an intelligent portable health monitoring apparatus, which is for the purpose of health surveillance. Specifically, the invention of an intelligent portable health monitoring apparatus comprises: a mainboard, and more than one set of photoelectric sensors connecting with the mainboard electronically, the more than one set of photoelectric sensors are able to adjust positions to cover the detected site properly by moving either the photoelectric transmitter or the photoelectric receiver, in order to acquire user's pulse and blood data. With the present invention of an intelligent portable health monitoring apparatus, it solves the problem of errors advantageously, which are induced by the differences of individual (Continued)

users during the noninvasive monitoring process, thus to present the users their accurate health conditions.

9 Claims, 3 Drawing Sheets

(51) Int. Cl.
  *A61B 5/024* (2006.01)
  *A61B 5/145* (2006.01)
(52) U.S. Cl.
  CPC ........ *A61B 5/14532* (2013.01); *A61B 5/6824* (2013.01); *A61B 5/0002* (2013.01); *A61B 5/681* (2013.01); *A61B 5/6814* (2013.01); *A61B 5/6825* (2013.01); *A61B 5/6829* (2013.01); *A61B 5/6831* (2013.01); *A61B 2562/0219* (2013.01)
(58) Field of Classification Search
  CPC ..... A61B 5/0002; A61B 5/681; A61B 5/6814; A61B 5/6825; A61B 5/6829; A61B 5/6831; A61B 2562/0219; A61B 5/02438; A61B 5/0205; A61B 5/021; A61B 5/02433; A61B 5/0816; A61B 5/1118; A61B 5/1455; A61B 5/14551; A61B 5/6802; A61B 5/6803; A61B 5/145
  See application file for complete search history.

(56) References Cited

U.S. PATENT DOCUMENTS

| | | | |
|---|---|---|---|
| 2010/0198027 A1* | 8/2010 | Dixon | A61B 5/14551 600/323 |
| 2016/0022210 A1* | 1/2016 | Nuovo | A61B 5/7445 600/301 |
| 2017/0347902 A1* | 12/2017 | Van Gool | A61B 5/02427 |
| 2018/0220968 A1* | 8/2018 | Funane | A61B 5/14553 |

FOREIGN PATENT DOCUMENTS

| | | |
|---|---|---|
| CN | 104287703 | 1/2015 |
| CN | 105997026 | 10/2016 |
| EP | 1 212 979 | 6/2002 |

\* cited by examiner

INTELLIGENT PORTABLE HEALTH MONITORING APPARATUS

This application is a national stage application of International Patent Application No. PCT/CN2017/085360, filed May 22, 2017, which claims priority to China Patent Application No. 201610412703.4, filed Jun. 13, 2016. The entirety of the aforementioned applications is incorporated herein by reference.

FIELD

The present invention is directed to an apparatus for health monitoring, especially as an intelligent portable health monitoring apparatus.

BACKGROUND

Nowadays a large portion of world population is composed of sub-healthy people, and the illnesses that sub-healthy people usually have include cardiovascular diseases, respiratory diseases, digestive system diseases, endocrine diseases, diabetes, early tumor symptoms, etc. For instance, the patients having cardiovascular disease may also have some other chronic diseases, and have to take several exams when visiting hospital. Therefore, the sub-healthy people with acute or chronic diseases have to spend significant time and money on the long-term health examinations and treatments, which affect their lives and work substantially.

However, the present available health monitoring products, for instance, an electrocardiogram monitor, having twelve leads to detect electrical signals of human body, is bulky and complicate in operation process, so normal people are unable to carry it conveniently and operate correctly. At present, the mature personal health monitoring products are mainly used to achieve such functions as hemomanometer, thermometer, oximetry, etc., which are under the demand to monitor multiple physiological parameters for people having acute or chronic diseases. Especially, because many lab tests need to take blood samples, such as blood glucose test, patients are highly looking forward to having an alternative noninvasive monitoring method for easy home operation, and to make less body wounds Comparing present personal health monitoring products and the examinations taken in hospital, the difference in accuracy is the main issue in multiple-parameter detections. Theoretically, the photoelectric sensors have an application scope different from the piezoelectric sensors and other types. The piezoelectric sensors test the amplitude of movement by muscle's contraction and relaxation, while photoelectric sensors detect the change of molecular states, for example, PPG infrared sensors are used to monitor blood oxygen level, in the range of visible light, platelet, oxyhemoglobin, bilirubin, and others in blood are the absorbents of surveillance. In the near infrared light range of 780 nm to 2500 nm, hemoglobin, glucose, hormones and other proteins have absorption peaks, and all of these substances are important detecting targets in the lab tests.

The position of light reflector of the photoelectric sensor affects whether the photoelectric receiver receiving the reflected signals or not, and the strength of the signals. Because of the differences of individual physical constitutions, and the differences in thickness from the subcutaneous blood vessels at different body parts to skin surface, if the distance between the photoelectric transmitter and the corresponding receiver of an intelligent portable health monitoring apparatus is fixed, many users may not detect the correct signals of physiological parameter, resulting in decreased practicability of the apparatus. Therefore, technical improvements are needed to improve the practicability of the personal portable intelligent health monitoring apparatus to satisfy the demands to monitor multiple physiological parameters at the same time for the diabetes, cardiovascular patients and others.

DETAILED DESCRIPTION

The main purpose of present invention is to provide an intelligent portable health monitoring apparatus, which is able to adjust to fit each individual user, and to monitor pulse, blood glucose, certain proteins and hormones efficiently and noninvasively, and to inform the users their health conditions in time.

In order to solve the described problems, the embodiments of present invention are provided as followings:

firstly, it provides an intelligent portable health monitoring apparatus, wherein said monitoring apparatus comprises:

a mainboard, and more than one set of photoelectric sensors connecting with the mainboard electronically;

the more than one set of photoelectric sensors are able to adjust positions to cover the detected site properly by moving either the photoelectric transmitter or the photoelectric receiver to acquire user's characteristic physiological data, the characteristic physiological data including pulse, blood pressure, blood glucose, hormones, haemoglobin, and enzymes.

Furthermore, each set of photoelectric sensors comprises:

a photoelectric transmitter; and a photoelectric receiver to receive signals transmitted from the photoelectric transmitter, setting at the same geometric plane as the photoelectric transmitter;

the photoelectric transmitter is implemented on a panel, and the corresponding photoelectric receiver is implemented on an extendable length-adjustable push-pull bar on the panel and by adjusting the position of the push-pull bar to arrange the distance between the set of photoelectric transmitter and receiver; or the photoelectric receiver is implemented on a panel, and the corresponding photoelectric transmitter is implemented on an extendable length-adjustable push-pull bar on the panel, and by adjusting the position of the push-pun bar to arrange the distance between the set of photoelectric transmitter and receiver; or the photoelectric transmitter is implemented on a panel, and the corresponding photoelectric receiver is implemented on an internal length-adjustable push-pull bar of the panel, and by adjusting the position of the push-pull bar to arrange the distance between the set of photoelectric transmitter and receiver; or the photoelectric receiver is implemented on a panel; and the corresponding photoelectric transmitter is implemented on an internal length-adjustable push-pull bar of the panel, and by adjusting the position of the push-pull bar to arrange the distance between the set of photoelectric transmitter and receiver.

Furthermore, the distance between the set of photoelectric transmitter and receiver is in the range of 0.5 cm to 5.5 cm.

Furthermore, the emitted light wavelength of the photoelectric transmitter is in the range of 300 nm to 2500 nm.

Furthermore, the intelligent portable health monitoring apparatus characterizes in that it also comprises:

a gyroscope sensor implemented on the mainboard, to collect position data and acceleration data.

Furthermore, the intelligent portable health monitoring apparatus characterizes in that it also comprises:

a storage module implemented on the mainboard, to store data collected by the photoelectric sensors and gyroscope; and a communication module implemented on the mainboard, to send data acquired by, the photoelectric sensors and gyroscope to a peripheral equipment through USB, wireless and/or Bluetooth methods;

the communication module is also able to receive data from the peripheral equipment.

Furthermore, the intelligent portable health monitoring apparatus characterizes in that it also comprises:

a display screen implemented on the mainboard, to display health information received by the communication module and the data acquired by the photoelectric sensors and gyroscope.

Furthermore, the outer covering of the intelligent portable health monitoring apparatus is provided a hole or holes for a strip band to be put through, the band used to wind round the detection part.

Furthermore, the intelligent portable health monitoring apparatus is either a hand-held monitoring apparatus, or a finger-pressed monitoring apparatus, or a wearable monitoring apparatus; and the wearable monitoring apparatus comprises of a wrist band, an ankle band, a hand strip, a watch, a head-strip, an arm-strip, etc.

The embodiments of the present invention have the following advantages:

the technical solutions of the intelligent portable health monitoring apparatus include implementing more than one set of photoelectric sensors to detect the changes of particular molecules in blood. In the visible light range, the absorbents in blood are platelet, oxyhemoglobin, bilirubin, and so on; in the near-infrared range from 780 urn to 2500 am, hemoglobin, glucose, hormones and other proteins have absorption peaks. Because all these substances are important exam targets in lab tests, it is necessary to use more than one set of photoelectric sensors to do noninvasive detection to monitor several characteristic physiological parameters simultaneously, and to solve the problem of errors induced by individual differences through using a length-adjustable push-pull bar, and to inform the users their health conditions in time.

DETAILED DESCRIPTION

To illustrate the technical problems to be solved, technical solutions and the advantages of the invention, more details and embodiments are described using FIGS. 1-6.

The embodiment of the invention, an intelligent portable health monitoring apparatus, is capable to monitor characteristic physiological parameters of users, and to inform the users their health conditions in time.

Figure 1:
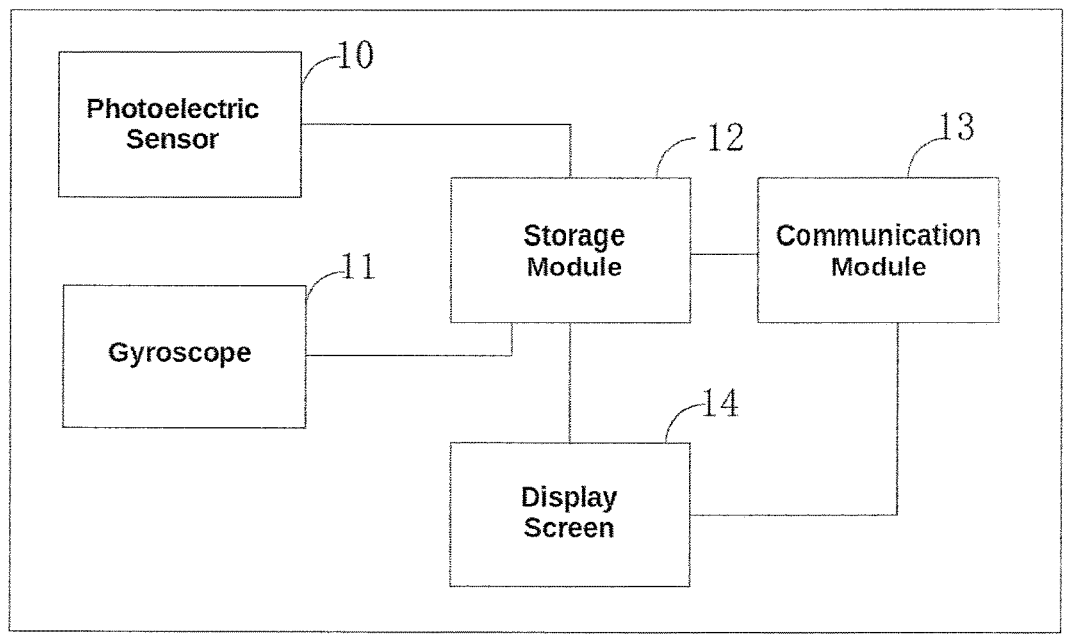
FIG. 1 is a topology map of the invention of an intelligent portable health monitoring apparatus.

In the implementation of the invention of an intelligent portable health monitoring apparatus, as shown in FIG. 1, characterized in that it comprises:

a mainboard; and more than one set of photoelectric sensors 10 connecting with the mainboard electronically, the more than one set of photoelectric sensors 10 are able to adjust positions to cover the detected site properly by moving either the photoelectric transmitter or the photoelectric receiver to acquire users' characteristic physiological data.

In the implementation of the invention of an intelligent portable health monitoring apparatus, characterized in that it comprises more than one set of photoelectric sensors, which are used to detect the changes of particular molecules. In the range of visible light, main absorbents in blood are platelet, oxyhemoglobin, bilirubin, etc. In the near infrared range from 780 nm to 2500 nm, hemoglobin, glucose, hormones and proteins have absorption peaks. Therefore, by employing more than one set of photoelectric sensors, multiple characteristic physiological parameters of users are monitored, and the users are able to know their health conditions in time.

And, the characteristic physiological parameters include but not limit to blood oxygen, heart rate, respiratory rate, blood pressure, blood glucose, enzymes and other proteins, hormones, etc.

Furthermore, each set of photoelectric sensors comprises:

a photoelectric transmitter; and a photoelectric receiver to receive signals transmitted from the photoelectric transmitter, setting at the same geometric plane as the photoelectric transmitter.

Figure 2:
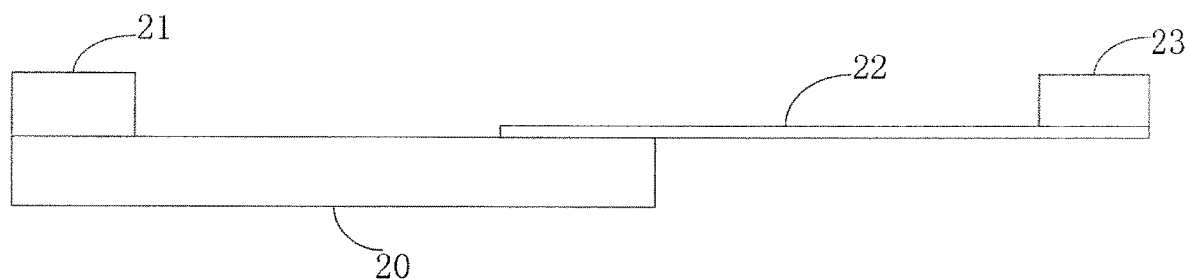
FIG. 2 is a topology map of photoelectric sensors arrangement.
Figure 3:
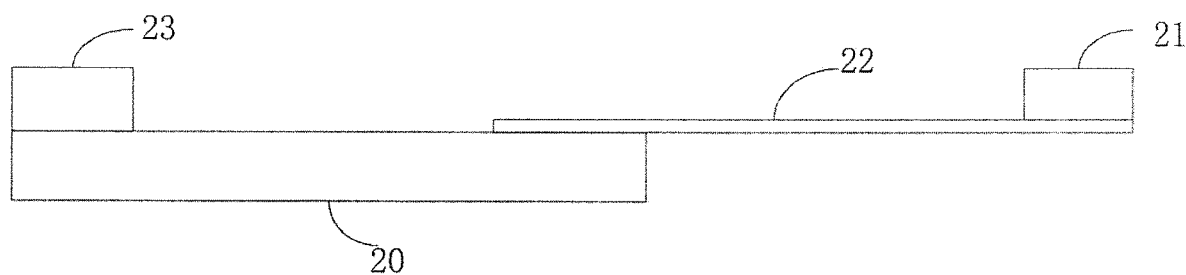
FIG. 3 is another example of topology map of photoelectric sensors arrangement.
Figure 4:
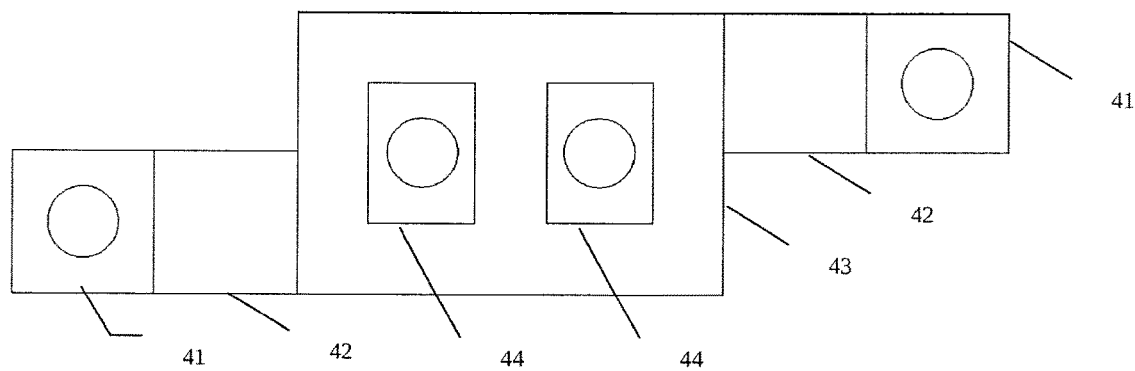
FIG. 4 is a vertical view of photoelectric sensors arrangement.

As shown in FIG. 2, the photoelectric transmitter 21 is implemented on a panel 20, and the corresponding photoelectric receiver 23 is implemented on an extendable length-adjustable push-pull bar 22 on the panel, and by adjusting the position of the push-pull bar 22 to arrange the distance between the photoelectric transmitter 21 and receiver 23; or as shown in FIG. 3, the photoelectric receiver 23 is implemented on a panel 20, and the corresponding photoelectric transmitter 21 is implemented on an extendable length-adjustable push-pull bar 22 on the panel, and by adjusting the position of the push-pull bar 22 to arrange the distance between the photoelectric transmitter 21 and receiver 23; or as shown in FIG. 4, the photoelectric transmitter 44 is implemented on a panel 43, and the corresponding photoelectric receiver 44 is implemented on an internal length-adjustable push-pull bar 42 of the panel 43, and by adjusting the position of the push-pull bar 42 to arrange the distance between the photoelectric transmitter 41 and receiver 44.

The position of the light reflector of the photoelectric sensor affects whether the photoelectric receiver can receive the reflected signals or not, and the strength of the signals. Because of the differences due to individual physical constitutions, and the differences of thickness between the subcutaneous blood vessels at different body parts and skin surface, so, if the distance between the photoelectric transmitter and the corresponding receiver of an intelligent portable health monitoring apparatus is fixed, many users may not be able to collect correct signals of physiological parameters, which lead to decreased practicability of the apparatus.

Figure 5:
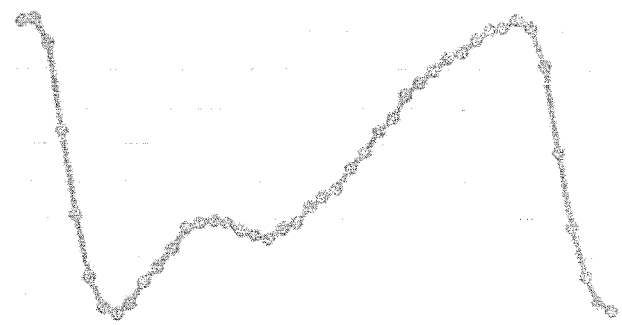
FIG. 5 is a schematic diagram of detected data vs. time by photoelectric sensor.

Therefore, as shown in FIG. 2 to FIG. 4, implementation examples of the invention have more than one photoelectric transmitter or receiver on the panel, and the paired receiver or transmitter, correspondingly, set at the end of a push-pull bar, and by adjusting the length of each bar, it is able to receive the strongest signals at the right distance, and every push-pull bar can implement more than one transmitter or receiver, and the photoelectric sensors are connected with the mainboard electronically. The invention of an intelligent portable health monitoring apparatus can be used conveniently for each user by adjusting the push-pull bar to receive the best signals, as shown in FIG. 5, and to reduce the occurrences of unable to receive right signals due to the individual differences when using an intelligent portable health monitoring apparatus, and to reduce the occurrences of wrong data processing and the problems of misleading users by the wrong data.

In some better implementation, the distances between the photoelectric transmitter and the paired receiver is in the range from 0.5 cm to 5.5 cm.

Furthermore, the emitted light wavelength of the photoelectric transmitter is in the range of 300 nm to 2500 nm.

Furthermore, as shown in FIG. 1, the intelligent portable health monitoring apparatus characterizes in that it also comprises:

a gyroscope sensor 11 implemented on the mainboard, to collect position data and acceleration data.

Furthermore, as shown in FIG. 1, the intelligent portable health monitoring apparatus characterizes in that it also comprises:

a storage module 12 implemented on the mainboard, to store physical characteristic data collected by the photoelectric sensors, and the position data and acceleration data collected by the gyroscope 11; and a communication module 13 implemented on the mainboard, to send the physical characteristic data collected by the photoelectric sensors and the position data and acceleration data collected by gyroscope 11 to a peripheral equipment. The communication module 13 sends the physical characteristic data through USB, wireless and/or Bluetooth methods to the peripheral equipment, so the peripheral equipment can analysis the physical characteristic data to get users' health information.

Furthermore, the communication module 1:3 is also used to receive health information analyzed from the physical characteristic data at the peripheral equipment.

As shown in FIG. 1, the intelligent portable health monitoring apparatus characterizes in that it also comprises:

a display screen 14 implemented on the mainboard, to display health information received by the communication module.

In some implementations of the intelligent portable health monitoring apparatus, it is programmed to power on or off at specified time to detect user's characteristic physiological data, and to send the user's characteristic physiological data out to a peripheral equipment via the communication module at specified time or at any time, and a designed software installed on the peripheral equipment is employed to analysis user's health conditions, and a display screen is used to display the data collected by photoelectric sensors and gyroscope and the analyzed health condition to the user, allowing the user w know their health condition in time.

In some implementations of the intelligent portable health monitoring apparatus, it comprises a wearable monitoring apparatus, or a wrist hand; or a watch, or a head-strip, or an arm-strip, or an unwearable separated device with more than one set of photoelectric sensors, for instance, a mobile phone, or a finger-pressed monitoring apparatus, or a handheld monitoring apparatus.

Furthermore, the intelligent portable health monitoring apparatus characterizes in that it also comprises: an outer covering of the apparatus having a hole or holes for a strip band to be put through, the strip band is used to wind round the detection site, being either a wrist band, or an arm band, or a head-strip, etc.

Furthermore, the intelligent portable health monitoring apparatus characterizes in that it also comprises different appearances of the outer covering, for example, a table-top detector with a supportive base, or a streamline shaped detector for easy hand holding.

Specifically, the implementation of the intelligent portable health monitoring apparatus characterizes in that it is a wrist band, when a user wearing it, the photoelectric sensors of the intelligent portable health monitoring apparatus are right on the radial artery at wrist; and when the intelligent portable health monitoring apparatus is an ankle strip, the photoelectric sensors are located upon the arteriae dorsalis pedis in the middle of instep when a user wearing it.

Figure 6:
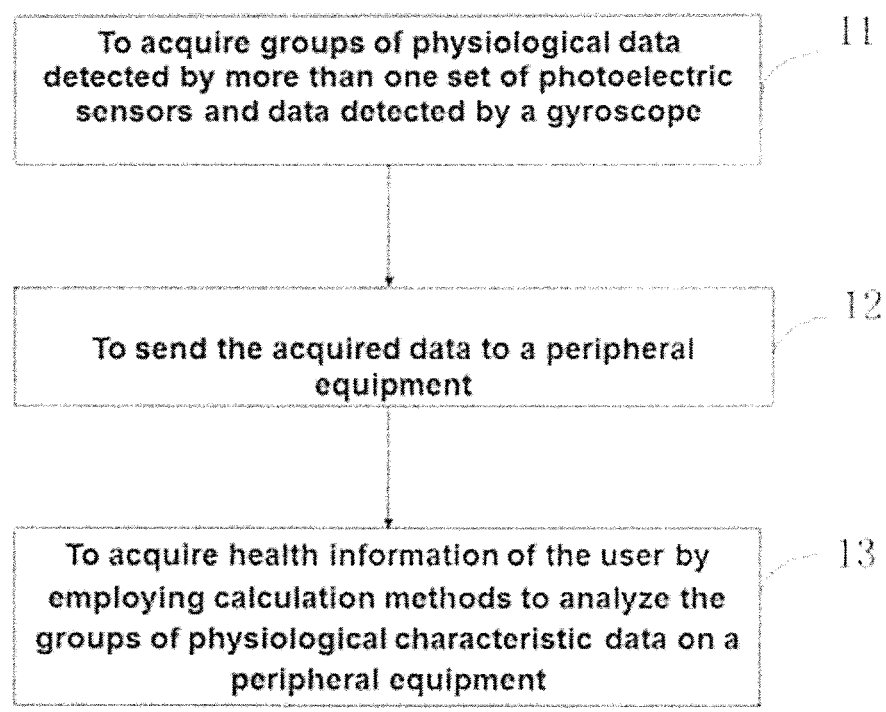
FIG. 6 is a workflow chart of an intelligent portable health monitoring apparatus.

As shown in FIG. 6, in some implementations of the working methods of the intelligent portable health monitoring apparatus, it comprises:

a step 11 of acquiring multiple characteristic physiological data collected by the more than one set of photoelectric sensors and location data collected by the gyroscope.

In some implementations of the intelligent portable health monitoring apparatus, it comprises more than one set of photoelectric sensors on the mainboard, which have working wavelength in the range from 300 nut to 2500 nm, used to collect multiple characteristic physiological parameters of the user, for example, as shown in FIG. 5 of a sample schematic diagram of data detected by a certain wavelength photoelectric sensor.

Furthermore, in step 12, it is to send the detected data to a peripheral equipment;

the peripheral equipment could be a server, a personal computer or a mobile terminal.

Furthermore, in step 13, the peripheral equipment is used to analyze users' health information by employing calculation methods on the received multiple characteristic physiological data.

The peripheral equipment are used to store archived health information in a data bank, and to analyze users' health conditions based on the received data in combination with the archived health information in the data bank.

In summary, the invention of an intelligent portable health monitoring apparatus characterizes in that it comprises more than one set of photoelectric sensors in the range of 300 urn to 2500 nm working wavelengths, to detect reflected light signals by particular molecules in pulse at some distance in the same plane as the corresponding sensor, and to acquire the characteristic physiological parameters of users. The said portable apparatus is able to measure pulse signals upon skin surface of finger artery, radial artery, arteriae dorsalis pedis, etc., and to collect gyroscopic data, then to send the data out to a peripheral equipment by USB, wireless and/or Bluetooth method, etc., to analyze multiple characteristic physiological parameters related to cardiovascular system, respiratory system, blood glucose, pancreas function, endocrine function, etc., to monitor multi characteristic physiological parameters conveniently for the user regarding as blood oxygen, heart rate, respiratory rate, blood pressure, blood glucose, pancreas function, endocrine function, etc., to realize instant monitor on body health changes, and to satisfy the demand of self-monitoring for those having acute and/or chronic illnesses, especially for patients having diabetes, cardiac disease, pancreatitis, etc, and to monitor personal physical conditions in coordination with their medical therapies.

The above described inventive embodiments are the better ways of implementing, and illustrated in details herein. Therefore, those of ordinary skill in the art will readily envision a variety of other means and/or structures for performing the function and/or, obtaining the results and/or one or more of the advantages described herein, and each of such variations and/or modifications is deemed to be within the scope of the inventive embodiments described herein.

The invention claimed is:

1. An intelligent portable health monitoring apparatus, comprising:
    a mainboard; and
    more than one set of photoelectric sensors connecting to the mainboard electronically,
    wherein the more than one set of photoelectric sensors are configured to adjust positions to cover a detected site properly by moving either a photoelectric transmitter or a photoelectric receiver to acquire a user's characteristic physiological data;
    wherein each set of photoelectric sensors comprises:
        a photoelectric transmitter; and
        a photoelectric receiver to receive signals transmitted from the photoelectric transmitter, setting at the same geometric plane as the photoelectric transmitter;
    wherein the characteristic physiological data includes pulse, blood pressure, blood glucose, and haemoglobin; and
    wherein the photoelectric transmitter is implemented on a panel, and the corresponding photoelectric receiver is implemented on an extendable length-adjustable push-pull bar of the panel, and wherein a distance between the photoelectric transmitter and the receiver is arranged by adjusting a position of the extendable length-adjustable push-pull bar, or
    wherein the photoelectric receiver is implemented on a panel, and the corresponding photoelectric transmitter is implemented on an extendable length-adjustable push-pull bar of the panel, and wherein a distance between the photoelectric transmitter and the receiver is arranged by adjusting a position of the extendable length-adjustable push-pull bar, or
    wherein the photoelectric transmitter is implemented on a panel, and the corresponding photoelectric receiver is implemented on an internal length-adjustable push-pull bar of the panel, and wherein a distance between the photoelectric transmitter and the receiver is arranged by adjusting a position of the internal length-adjustable push-pull bar, or
    wherein the photoelectric receiver is implemented on a panel, and the corresponding photoelectric transmitter is implemented on an internal length-adjustable push-pull bar of the panel, and wherein a distance between the photoelectric transmitter and the receiver is arranged by adjusting the position of the internal length-adjustable push-pull bar.

2. The intelligent portable health monitoring apparatus according to claim 1,
    wherein the distance between each set of photoelectric transmitter and receiver is in a range of 0.5 cm to 5.5 cm.

3. The intelligent portable health monitoring apparatus according to claim 1,
    wherein the emitted light wavelength of the photoelectric transmitter is in a range of 300 nm to 2500 nm.

4. The intelligent portable health monitoring apparatus according to claim 1, further comprising:
    a gyroscope sensor implemented on the mainboard, to collect position data and acceleration data.

5. The intelligent portable health monitoring apparatus according to claim 1, further comprising:
    a storage module implemented on the mainboard, to save data collected by the photoelectric sensors and gyroscope; and
    a communication module implemented on the mainboard, to send data acquired by the photoelectric sensors and gyroscope to a peripheral equipment through USB, wireless and/or Bluetooth methods;
    wherein the communication module is configured to receive data from the peripheral equipment.

6. The intelligent portable health monitoring apparatus according to claim 5, further comprising:
    a display screen implemented on the mainboard to display health information received by the communication module and the data acquired by the photoelectric sensors and gyroscope.

7. The intelligent portable health monitoring apparatus according to claim 1,
    wherein the intelligent portable health monitoring apparatus is either a hand-held monitoring apparatus, or a finger-pressed monitoring apparatus, or a wearable monitoring apparatus; and
    wherein the wearable monitoring apparatus comprises of a wrist band, an ankle band, a hand strip, a watch, a head-strip, or an arm-strip.

8. The intelligent portable health monitoring apparatus according to claim 1,
    wherein the distance between the photoelectric transmitter and the receiver is in a range of 0.5 cm to 5.5 cm.

9. The intelligent portable health monitoring apparatus according to claim 1, wherein the emitted light wavelength of the photoelectric transmitter is in a range of 300 nm to 2500 nm.

* * * * *